(12) United States Patent
Yliperttula et al.

(10) Patent No.: US 9,631,177 B2
(45) Date of Patent: Apr. 25, 2017

(54) DRUG DELIVERY COMPOSITIONS

(75) Inventors: Marjo Yliperttula, Espoo (FI); Patrick Laurén, Espoo (FI); Madhushree Bhattacharya, Helsinki (FI); Yanru Lou, Helsinki (FI); Antti Laukkanen, Helsinki (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

(21) Appl. No.: 13/881,982

(22) PCT Filed: Oct. 26, 2011

(86) PCT No.: PCT/FI2011/050941
§ 371 (c)(1),
(2), (4) Date: Aug. 19, 2013

(87) PCT Pub. No.: WO2012/056111
PCT Pub. Date: May 3, 2012

(65) Prior Publication Data
US 2013/0330379 A1    Dec. 12, 2013

(30) Foreign Application Priority Data

Oct. 27, 2010 (FI) .................................. 20106121

(51) Int. Cl.
| | | |
|---|---|---|
| *A61K 47/26* | (2006.01) | |
| *C12N 5/071* | (2010.01) | |
| *A61K 9/06* | (2006.01) | |
| *A61K 47/38* | (2006.01) | |
| *A61L 27/20* | (2006.01) | |
| *A61L 27/36* | (2006.01) | |
| *A61L 27/38* | (2006.01) | |
| *A61L 27/52* | (2006.01) | |
| *C08J 3/075* | (2006.01) | |
| *C08L 1/02* | (2006.01) | |
| *C12N 5/00* | (2006.01) | |
| *C12N 11/04* | (2006.01) | |
| *C12N 11/12* | (2006.01) | |
| *C08L 97/02* | (2006.01) | |
| *C12N 5/0735* | (2010.01) | |
| *C12N 5/079* | (2010.01) | |

(52) U.S. Cl.
CPC .............. *C12N 5/0671* (2013.01); *A61K 9/06* (2013.01); *A61K 47/26* (2013.01); *A61K 47/38* (2013.01); *A61L 27/20* (2013.01); *A61L 27/3637* (2013.01); *A61L 27/38* (2013.01); *A61L 27/52* (2013.01); *C08J 3/075* (2013.01); *C08L 1/02* (2013.01); *C08L 97/02* (2013.01); *C12N 5/0068* (2013.01); *C12N 5/0606* (2013.01); *C12N 5/067* (2013.01); *C12N 5/0621* (2013.01); *C12N 5/0672* (2013.01); *C12N 11/04* (2013.01); *C12N 11/12* (2013.01); *C08J 2301/02* (2013.01); *C08J 2389/00* (2013.01); *C12N 2533/78* (2013.01)

(58) Field of Classification Search
USPC ....................................... 424/93.7, 445, 488
See application file for complete search history.

(56) References Cited

U.S. PATENT DOCUMENTS

| | | | |
|---|---|---|---|
| 5,405,953 A * | 4/1995 | Banker et al. .................. 536/56 |
| 5,558,861 A | 9/1996 | Yamanaka | |
| 6,602,994 B1 | 8/2003 | Cash et al. | |
| 2007/0053960 A1 | 3/2007 | Brown, Jr. | |
| 2007/0275458 A1 | 11/2007 | Gouma | |
| 2009/0028927 A1 * | 1/2009 | Wan et al. .................... 424/445 |
| 2009/0305412 A1 | 12/2009 | Ying | |
| 2010/0065236 A1 | 3/2010 | Henriksson et al. | |
| 2010/0172889 A1 | 7/2010 | Catchmark | |
| 2010/0233234 A1 | 9/2010 | Arinzeh et al. | |
| 2010/0233245 A1 * | 9/2010 | Narayana ...................... 424/443 |
| 2011/0015387 A1 | 1/2011 | Schuth et al. | |
| 2011/0198282 A1 | 8/2011 | Chu et al. | |
| 2013/0011385 A1 | 1/2013 | Li et al. | |

FOREIGN PATENT DOCUMENTS

| | | |
|---|---|---|
| CN | 1718172 A | 1/2006 |
| CN | 1730734 A | 2/2006 |
| CN | 1973029 A | 5/2007 |
| CN | 101392246 A | 3/2009 |
| JP | 2008001728 A | 1/2008 |
| JP | 2008308802 A | 12/2008 |
| JP | 2009502242 A | 1/2009 |
| JP | 2009126837 A | 6/2009 |
| JP | 2009523849 A | 6/2009 |
| JP | 2010007010 A | 1/2010 |
| JP | 2011057746 A | 3/2011 |
| WO | 2007/066222 A1 | 6/2007 |

(Continued)

OTHER PUBLICATIONS

Hubbe et al., "Cellulosic Nanocomposites: A Review." BioResources 2008:3(3);929-980.*
Michailova et al., "Rheological characteristics and diffusion processes in mixed cellulose hydrogel matrices." J. Drug Del. Sci. Tech 2005:15(6);443-449.*
Cherian et al., "Isolation of nanocellulose from pineapple leaf fibres by steam explosion." Carbohydrate Polymers 81 (2010) 720-725.*
Hoare et al., "Hydrogels in drug delivery: Progress and challenges." Polymer 49 (2008) 1993-2007.*
Czaja W Et Al: "Microbial cellulose-the natural power to heal wounds", Biomaterials, vol. 27. No. 2. Jan. 2006, pp. 145-151, XP025096958, ISSN: 0142-9612. 001: 10.1016/J.Biomateriais. 2005.07.035 [retrieved on Jan. 1, 2006].

(Continued)

*Primary Examiner* — Walter Webb
(74) *Attorney, Agent, or Firm* — Nixon Peabody LLP; Leena Karttunen Contarino; Elizabeth W. Baio

(57) ABSTRACT

The present invention relates material that is useful in drug delivery compositions. The material comprises cellulose nanofibers and/or derivatives thereof, wherein the cellulose nanofibers are in a form of a hydrogel or membrane. The invention also provides methods for producing these materials and compositions and uses thereof.

16 Claims, 5 Drawing Sheets

(56) References Cited

FOREIGN PATENT DOCUMENTS

| | | |
|---|---|---|
| WO | 2009/126106 A1 | 10/2009 |
| WO | 2009126980 A1 | 10/2009 |
| WO | 2010092239 A1 | 8/2010 |
| WO | 2010/115785 A1 | 10/2010 |

OTHER PUBLICATIONS

Müller A et al: "Bacterial nanocellulose wound dressing as drug delivery system", American Chemical Society. Abstracts of Paper; 239th National Meeting of the American Chemical Society, US; San Francisco. CA. US, vol. 239, Cell-22, Mar. 21, 2010, XP008151040, ISSN: 0065-7727.

Wiegand C et al: "HaCaT keratinocytes in co-culture with *Staphylococcus aureus* can be protected from bacterial damage by polihexanide", Wound Repair & Regeneration, vol. 17. No. 5, Sep. 2009, pp. 730-738. XP55016133, ISSN: 1067-1927, DOI: 10.1111/j.1524-475X.2009.00536.x.

Elzinga G et al: "Clinical evaluation of a PHMB-impregnated biocellulose dressing on paediatric lacerations", Journal of Wound Care, vol. 20. No. 6. Jun. 2011, pp. 280-284. XP55025495, ISSN: 0969-0700.

Valo H et al: " Immobilization of protein-coated drug nanoparticles in nanofibrillar cellulose matrices-Enhanced stability and release", Journal of Controlled Release, vol. 156. No. 3, Dec. 2011, pp. 390-397. XP55025318, ISSN: 0168-3659. DOI: 10.1016/j.jconrel.2011.07.016 [retrieved on Jul. 23, 2011] online publication Jul. 23, 2011.

Trovatti E et al: "Biocellulose Membranes as Supports for Dermal Release of Lidocaine", Biomacromolecules, vol. 12, No. 11, Nov. 14, 2011, pp. 4162-4168. XP55025497, ISSN: 1525-7797. DOI: 10.1021/bm201303r [retrieved on Oct. 16, 2011] online publication Oct. 16, 2011.

International Search Report of PCT/FI2011/050941.

International Preliminary Report on Patentability of PCT/FI2011/050941.

Deguchi, S. et al. Preparation and characterisation of nanofibrous cellulose plate as a new solid support for microbial culture. Soft Matter, 2007, vol. 3, No. 9, p. 1170-1175.

Ping, W. et al. 'Study on the feasibility of bacterial cellulose as tissue engineering scaffold', Multi-Functional Materials and Structures II, 2nd International Conference on Multi-Functional Materials and Structures, Advanced Materials Research, 2009, vols. 79-82, p. 147-150.

Evenou F et al: "Microfibrillated cellulose sheets coating oxygen-permeable PDMS membranes induce rat hepatocytes 3D aggregation into stably-attached 3D hemispheroids."; J. Biomater. Sci. Polym. Ed. 2011 , vol. 22, No. 11, p. 1509-1522. XP002674465; and Database Medline [Online]; US National Library of Medicine (NLM); Bethesda. MD, US; Jul. 12, 2010; Database accession No. NLM20626957 abstract.

Recouvreux, D.O.S. et al. Novel three-dimensional cocoon-like hydrogels for soft tissue regeneration. Mater. Sci. Eng. C, Mar. 2011, vol. 31, No. 2, p. 151-157. Available online (Epub) Aug. 13, 2010.

Bäckdahl H et al: "Mechanical properties of bacterial cellulose and interactions with smooth muscle cells", Biomaterials, vol. 27. No. 9. Mar. 2006, pp. 2141-2149. XP025097665, ISSN: 0142-9612, DOI: 10.1016/J.Biomaterials.2005.10.026 [retrieved on Mar. 1, 2006].

Office Action with Search Report dated Jun. 6, 2011 of FI 20106121.

Bodin A et al: "Modification of Nanocellulose with a Xyloglucan-RGD Conjugate Enhances Adhesion and Proliferation of Endothelial Cells: Implications for Tissue Engineering", Biomacromolecules, vol. 8. No. 12, pp. 3697-3704. XP55025397, ISSN: 1525-7797, DOI: 10.1021/bm070343q published Nov. 2007.

Czaja W K Et Al: "The Future Prospects of Microbial Cellulose in Biomedical Applications", Biomacromolecules, vol. 8, No. 1, Jan. 2007, pp. 1-12, XP55025315, ISSN: 1525-7797, DOI: 10.1021/bm060620d [retrieved on Dec. 1, 2006] p. 9-p. 10.

Database WPI, Week 200930, Thomson Scientific. London. GB; AN 2009-H01547; XP002674558; -& CN 101 392 246 A (Univ Northeast Electric Power) Mar. 25, 2009 abstract.

Grande C Jet Al: "Nanocomposites of bacterial cellulose/hydroxyapatite for biomedical applications", Acta Biomaterialia, vol. 5. No. 5. Jun. 2009. pp. 1605-1615. XP026090223, ISSN: 1742-7061. DOI: 10.1016/J.ACTBI0.2009.01.022 [retrieved on Jan. 31, 2009].

Sanchavanakit N et al: "Growth of Human Keratinocytes and Fibroblasts on Bacterial Cellulose Film", Biotechnology Progress, vol. 22. No. 4, Aug. 4, 2006, pp. 1194-1199. XP55025385, ISSN: 8756-7938, DOI: 10.1021/bp0600350.

Svensson A et al: "Bacterial cellulose as a potential scaffold for tissue engineering of cartilage", Biomaterials, vol. 26. No. 4. Feb. 2005, pp. 419-431, XP025280897, ISSN: 01429612, DOI: 10.1016/J. Biomaterials, 2004.02.049 [retrieved on Feb. 1, 2005].

Mueller et al., "Bacterial nanocellular wound dressing as drug delivery system", Abstract of paper; 239th National Meeting of the American Chemical Society, vol. 239, P. Cell-22 (Mar. 21, 2010).

Cai, Z. et al.; "Preparation and Characterization of Novel Bacterial Cellulose/Gelatin Scaffold for Tissue Regeneration Using Bacterial Cellulose Hydrogel"; J. Nanotech. in Eng. and Med. May 2010, vol. j / 021002-1-021002-6 (6 pages).

Sigma-Aldrich; Safety Data Sheet for "Sigmacell Cellulose"; vers. 3.6, Rev. Aug. 13, 2014 (7 pages).

Daicel FineChem Ltd.; "Celish / Tiara (Microfibrillated products)"; retrieved from <http://www.daicelfinechem.jp/en/business/wspdiv/celish.html> on Apr. 14, 2016 (3 pages).

Deguchi, S. et al.; "Nanofibrous Cellulose as Novel Solid Support for Microbial Culture"; Polymer Preprints, Japan vol. 57, No. 1 (2008) (3 pages); in Japanese and English.

Mugishima, H. et al.; "Relationship between morphologies and functions of osteoblast cultured on cellulose nanofibers materials"; Fiber Preprints, Japan vol. 65 (Jun. 16, 2010), No. 1 (Annual Meeting) (8 pages); in Japanese and English.

Henriksson, M. et al.; "An environmentally friendly method for enzyme-assisted preparation of microfibrillated cellulose (MFC) nanofibers"; Euro. Polymer J. 43 (2007) 3434-3441; available online Jun. 8, 2007 at www.sciencedirect.com (8 pages).

Acumedia Manufacturers, Inc.; Technical sheet for "LB Broth, Lennox (7290)"; PI 7290, Rev. Nov. 4, 2010 (2 pages).

Borges, A. C. et al.; "Nanofibrillated cellulose composite hydrogel for the replacement of the nucleus pulposus"; Acta Biomaterialia 7 (2011) pp. 3412-3421; available online May 27, 2011 (10 pages).

Paakko, M. et al.; "Enzymatic Hydrolysis Combined with Mechanical Shearing and High-Pressure Homogenization for Nanoscale Cellulose Fibrils and Strong Gels"; Biomacromolecules 2007, 8, pp. 1934-1941; published May 3, 2007; XP003026928 (8 pages).

Klemm, D. et al.; "Nanocelluloses as Innovative Polymers in Research and Application"; Adv. Polym. Sci. 2006; 205:49-96; DOI 10.1007 12_097; Springer-Verlag Berlin Heidelberg 2006; published online Aug. 30, 2006 (48 pages).

\* cited by examiner

DRUG DELIVERY COMPOSITIONS

CLAIM FOR PRIORITY

This application claims priority under 35 USC 371 to International Application No. PCT/FI2011/050941, filed on Oct. 26, 2011, which claims priority to Finnish Patent Application No. 20106121, filed Oct. 27, 2010, each of which is hereby incorporated by reference in its entirety.

FIELD OF THE INVENTION

The invention relates to drug delivery compositions comprising cellulose nanofibers or derivatives thereof.

BACKGROUND OF THE INVENTION

Health care remains at the foremost frontiers for scientific research. The need to discover and develop cost-effective and safer medications is ever increasing.

Hydrogels, both of synthetic and natural origin have emerged for example as suitable scaffolds for 3D cell culture. The network of interconnected pores in hydrogels allows for retention of a large amount of biological fluid, facilitates transport of oxygen, nutrients and waste. Furthermore, most hydrogels can be formed under mild cytocompatible conditions and the biological properties can be modulated by surface chemistry. Engineered hydrogels with modified mechanical, chemical and biological properties have the potential to mimic the ECM and thus establish their utility in 3D cell culture. Commercial products for 3D cell culturing are for example PuraMatrix™ (3DM Inc.) and Matrigel (BD Biosciences). PuraMatrix™ is a hydrogel of self-assembled peptide nanofibers wich resembles the structure of natural fibrillar collagen in ECM with fiber diameter 5-10 nm. It has also high water content, typically 99.5%. U.S. Pat. No. 7,449,180 and WO 2004/007683 disclose peptide hydrogels. Matrigel is gelatinous protein mixture secreted by mouse tumor cells. The mixture resembles the complex extracellular environment found in many tissues and is used by cell biologists as a substrate for cell culture. MaxGel™ ECM Matrix (Sigma-Aldrich), which includes a mixture of human ECM components, forms a gel in ambient temperature.

Conventional bacterial cellulose has been used in wound healing membranes and as a scaffold in cell culture. The limitation in the use of bacterial cellulose is the inherent structure of the fermented material; upon cultivation, bacterial cellulose is formed as very tight membranes in air water interphase in the fermenter.

Hydrogel materials are widely used in culturing tasks where hydrophilic supporting material is needed, for example agar type hydrocolloids are used in plant cell, bacterial, and fungi culturing for various microbiological purposes.

U.S. Pat. No. 5,254,471 discloses a carrier for culturing cells made of ultra fine fibers. WO 2009/126980 discloses cellulose-based hydrogel, which contains cellulose exhibiting an average degree of polymerization of 150-6200.

BRIEF DESCRIPTION OF THE INVENTION

There is a clear need for hydrogel matrix or carrier useful in drug delivery compositions.

An object of the present invention is to provide a novel approach for drug delivery compositions. The objects of the invention are achieved by a drug delivery composition comprising cellulose nanofibers and/or derivatives thereof and at least one drug substance or medicament. The characteristic features of the invention are stated in the independent claims. The preferred embodiments are disclosed in the dependent claims.

The present invention is based on the use of cellulose nanofibers and/or derivatives thereof in a hydrogel matrix.

The present inventor surprisingly found out that hydrogels composed of cellulose nanofibers (CNF) and/or derivatives thereof can be used, even without any modifications, in drug delivery compositions. CNF hydrogel is an optimal biomaterial for drug delivery in vivo.

The present inventors describe particularly the physical and biocompatibility properties of plant derived CNF hydrogel. Plant cellulose is extensively used in the paper and textile industry and is abundant naturally. The native cellulose nanofiber hydrogel is opaque. Chemical modification of cellulose pulp prior to mechanical disintegration gives rise to optically transparent hydrogels.

The present invention is based on experimental studies on hydrogels composed of cellulose nanofibers (CNF) and/or derivatives thereof, which are dispersed in aqueous environment. The nanofibers are highly hydrophilic due to hydroxyl functionalities of cellulose polymers and partly covered with hemicellulose polysaccharides.

Accordingly the present invention provides a drug delivery composition comprising cellulose nanofibers and/or derivatives thereof, wherein the cellulose nanofibers are in a form of a hydrogel or membrane.

A significant advantage of the present invention is that drugs can be maintained in the biomaterial media without additives. The drug substance particles are evenly dispersed in the media/matrix containing cellulose nanofibers or a derivative thereof. The homogenous distribution of the drug in the cellulose nanofibers and/or aderivatives thereof is a prerequisite for the material to function as supporting or carrier media for drugs.

Further advantages of the present invention include: cellulose nanofibers and/or derivatives thereof are inert and give no fluorescent background. The media comprising cellulose nanofibers and/or derivatives thereof can be injected. Injectability is explained by the rheological properties. The injection can be performed so that the drug stays stable inside matrix and is homogeneously distributed in the matrix after injection.

Figure 6:
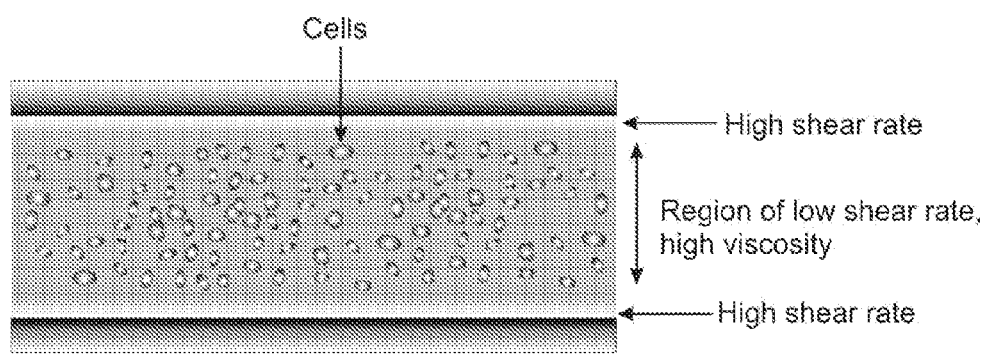

FIG. 6 depicts schematic presentation of CNF hydrogel containing cells, flowing in a needle. High shear rate region (low viscosity) is located at the gel-needle interface and low shear rate region (very high viscosity) is located in the middle of the needle.

Figure 7:
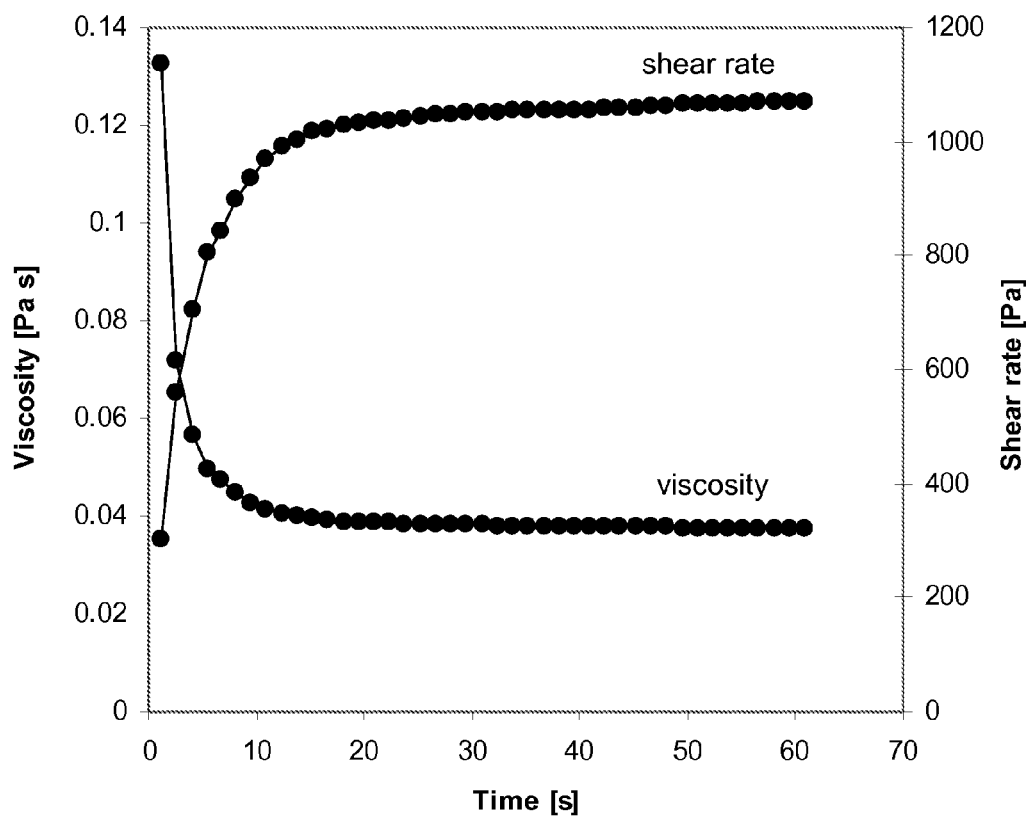

FIG. 7 depicts evolution of shear rate and viscosity when a 0.7% native CNF hydrogel was sheared in a rheometer in concentric cylinder geometry at a constant stress of 40 Pa.

Figure 8:
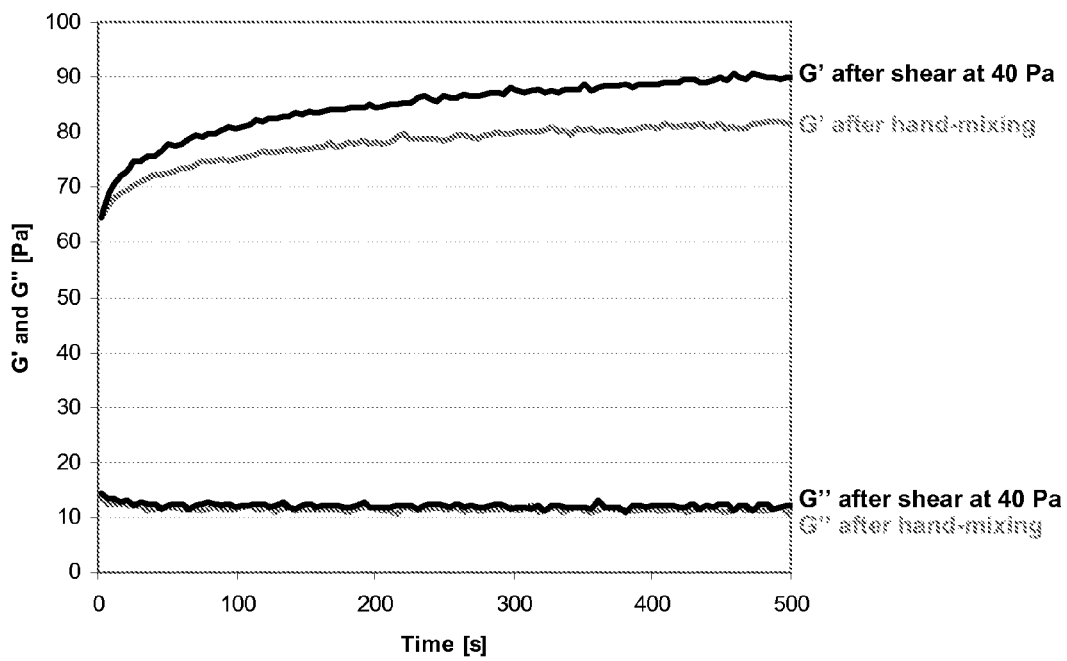

FIG. 8 depicts structure recovery of a 0.7% native CNF hydrogel dispersion after shearing at high shear-rate as compared with after gentle mixing with a glass rod.

Figure 9:
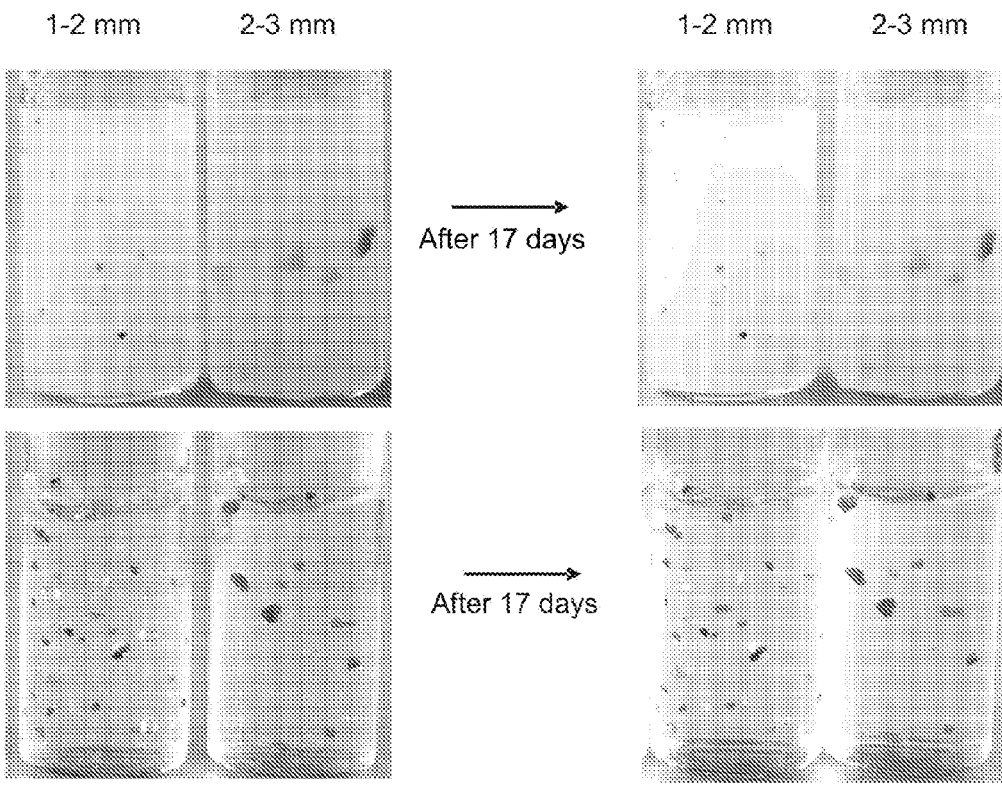

FIG. 9 depicts stability of two gravel suspensions in 0.5% native CNF hydrogel, (top row) and in 0.5% transparent CNF hydrogel (bottom row) for 17 days period. The gravel was CEN Standard sand (EN 196-1) with average particle size 1-2 mm and 2-3 mm. The samples were stored at room temperature.

Figure 10:
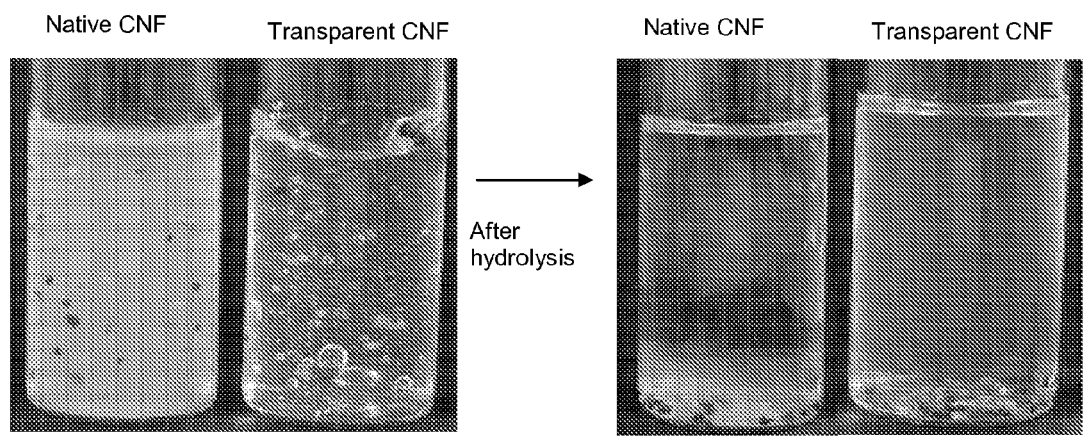

FIG. 10 depicts the influence of enzymatic hydrolysis on the suspension ability of cellulose nanofiber gels. The gravel was CEN Standard sand (EN 196-1) with average particle size 1-2 mm.

DETAILED DESCRIPTION OF THE INVENTION

The present invention relates to a drug delivery composition comprising cellulose nanofibers and/or derivatives thereof, wherein the cellulose nanofibers or derivative thereof are in a form of a hydrogel or membrane. Cellulose nanofibers or derivatives thereof can be obtained from non-animal based material such as raw material comprising plant material or microbial cellulose or derived from bacterial fermentation processes, commonly known as bacterial cellulose (BC).

Unless otherwise specified, the terms, which are used in the specification and claims, have the meanings commonly used in the field. Specifically, the following terms have the meanings indicated below.

The term "drug delivery composition" refers to a material comprising cellulose nanofibers and/or derivatives of cellulose nanofibers, and drug or medicament. Said material is suitable for the use in the delivery of drugs or medicaments for humans and animals. Cellulose nanofibers can be in a form or a hydrogel or membrane. Said composition can further contain various additives.

The term "cellulose raw material" refers to any cellulose raw material source that can be used in production of cellulose pulp, refined pulp, or cellulose nanofibers. The raw material can be based on any plant material that contains cellulose. The raw material can also be derived from bacterial fermentation processes. Plant material may be wood. Wood can be from softwood tree such as spruce, pine, fir, larch, douglas-fir or hemlock, or from hardwood tree such as birch, aspen, poplar, alder, eucalyptus or acacia, or from a mixture of softwoods and hardwoods. Non-wood material can be from agricultural residues, grasses or other plant substances such as straw, leaves, bark, seeds, hulls, flowers, vegetables or fruits from cotton, corn, wheat, oat, rye, barley, rice, flax, hemp, manilla hemp, sisal hemp, jute, ramie, kenaf, bagasse, bamboo or reed.

The cellulose raw material may also be derived from cellulose-producing micro-organism whereby it is called microbial cellulose. "Cellulose nanofibers" can be directly isolated from certain fermentation processes. The cellulose-producing micro-organism may be of the genus *Agrobacterium, Rhizobium, Pseudomonas* or *Alcaligenes*, suitably of the genus *Acetobacte*, such as the species *Acetobacter xylinum* or *Acetobacter pasteurianus*.

The term "cellulose pulp" refers to cellulose fibers, which are isolated from any cellulose raw material using chemical, mechanical, thermo-mechanical, or chemi-thermo-mechanical pulping processes. Typically the diameter of the fibers varies between 15-25 µm and length exceeds 500 µm, but the present invention is not intended to be limited to these parameters.

The term "cellulose nanofiber" refers to a collection of isolated cellulose nanofibers (CNF) or nanofiber bundles derived from cellulose raw material or cellulose pulp. Nanofibers have typically high aspect ratio: the length might exceed one micrometer while the number-average diameter is typically below 200 nm. The diameter of nanofiber bundles can also be larger but generally less than 1 µm. The smallest nanofibers are similar to so called elementary fibrils, which are typically 2-12 nm in diameter. The dimensions of the fibrils or fibril bundles are dependent on raw material and disintegration method. The cellulose nanofibers may also contain some hemicelluloses; the amount is dependent on the plant source.

Mechanical disintegration of cellulose raw material, cellulose pulp, or refined pulp is carried out with suitable equipment such as a refiner, grinder, homogenizer, colloider, friction grinder, ultra-sound sonicator, fluidizer such as microfluidizer, macrofluidizer or fluidizer-type homogenizer. As a result cellulose nanofibers are obtained. Preferably cellulose raw material, including microbial cellulose is mechanically disintegrated.

"Cellulose nanofibers" or "cellulose nanofibers or a derivative thereof" can also be any chemically or physically modified derivate of cellulose nanofibers or nanofiber bundles. The chemical modification may be based for example on carboxymethylation, oxidation, (for example TEMPO-oxidation), esterification, or etherification reaction of cellulose molecules. Modification may also be realized by physical adsorption of anionic, cationic, or non-ionic substances or any combination of these on cellulose surface. The described modification can be carried out before, after, or during the production of cellulose nanofibers. Certain modifications may lead to CNF materials that are degradable in human body.

Suitably the cellulose raw material such as cellulose pulp is pretreated with acid and base prior to the mechanical disintegration. The pretreatment is effected by subjecting the cellulose pulp to acid treatment, preferably with hydrochloric acid for removing any positively charged ions having a charge more than +1, followed by treatment with an inorganic base containing positively charged ions having a charge +1, preferably NaOH, where $Na^+$ ions replace the earlier ions. This pretreatment provides the "cellulose nanofibers" excellent gelling properties and transparency. This pretreated product is referred to as acid-base pretreated or ion exchanged "cellulose nanofibers".

Microbial purity of the "cellulose nanofibers" is often essential for the product. Therefore, the "cellulose nanofibers" may be sterilized in a hydrogel or membrane form. In addition to that it is important to minimize the microbial contamination of the product before and during the mechanical disintegration, such as fibrillation. Prior to fibrillation, it is advantageous to aseptically collect the cellulose pulp from the pulp mill immediately after bleaching stage when the pulp is still sterile.

There are several widely used synonyms for "cellulose nanofibers". For example: nanocellulose, nanofibrillated cellulose (CNF), nanofibrillar cellulose, cellulose nanofiber, nano-scale fibrillated cellulose, microfibrillar cellulose, microfibrillated cellulose (CNF), or cellulose microfibrils.

In addition, cellulose nanofibers produced by certain microbes has also various synonyms, for example bacterial cellulose (BC), microbial cellulose (MC), biocellulose, nata de coco (NDC), or coco de nata.

Cellulose nanofibers described in this invention is not the same material as so called cellulose whiskers, which are also known as: cellulose nanowhiskers, cellulose nanocrystals, cellulose nanorods, rod-like cellulose microcrystals or cellulose nanowires. In some cases, similar terminology is used for both materials, for example by Kuthcarlapati et al. (Metals Materials and Processes 20(3):307-314, 2008) where the studied material was called "cellulose nanofiber" although they clearly referred to cellulose nanowhiskers. Typically these materials do not have amorphous segments along the fibrillar structure as cellulose nanofibers, which lead to more rigid structure. Cellulose whiskers are also shorter than cellulose nanofibers; typically the length is less than one micrometer.

The dimensions of individual cellulose nanofibers are quite close to aforementioned dimensions of collagen fibers in ECM, i.e. 4-10 nm.

In the experiments of the present invention, two kinds of cellulose nanofibers were used: opaque native CNF and optically transparent CNF, which was TEMPO-oxidized cellulose. Detailed description of the materials is presented in the Examples, Materials and methods section.

The term "cellulose nanofiber hydrogel" refers to aqueous dispersion of cellulose nanofibers.

The term "cellulose nanofiber membrane" refers to wet or dry sheet-like formation of cellulose fibers. The membranes are typically produced by filtration of dilute cellulose nanofiber dispersion with vacuum filtration apparatus with a proper filter. Solvent casting may also be used to obtain aforementioned membrane structures. The obtained membrane can be used as such in wet state or dried prior use.

The cellulose nanofibers or a derivative thereof of the present invention can comprise chemically or physically modified derivates of cellulose nanofibers or nanofiber bundles.

The drug delivery compositions of the present invention are based on the properties of the hydrogel, particularly the injectability of the hydrogel. Said compositions are suitable for the injection of drugs in CNF hydrogel in intraocular, intramuscular, or in subcutaneous treatment, however the properties of the hydrogel make it also very suitable for topical products. The drug delivery composition may comprise one or more active drug substances or medicaments incorporated in the cellulose nanofiber hydrogel. Said drug substances may be selected from drug substances and medicaments suitable for topical use, for intramuscular use, for intraocular use, for subcutaneous use and for use in connection with surgery. Examples of such drugs are hormones, anesthetic, chemotherapeutic, anti-inflammatory, antimicrobial, analgesic, drug substances and medicaments, as well as biotechnical and biological drugs, peptide and protein drugs.

The drug delivery composition of the present invention may further comprise one or more suitable and pharmaceutically acceptable additives generally used in topical, intramuscular, intraocular, and subcutaneous preparations, for example preservatives, emollients, absorbents, protective agents, demulcents, antioxidants, buffering agents, moisturizers, skin-penetration enhancers, solubilizers etc well known to a man skilled in the art.

The drug delivery composition is suitable as a topical product for the local delivery of drug substances, as a topical product for the systemic delivery of drug substances which are readily absorbed through the skin, for subcutaneous delivery of drugs and for injectable drugs, which are directly administered to the site or organ where the effect is desired. The composition is also particularly suitable for dental applications, and for intraocular, intravitreal, intramuscular and subcutaneous delivery of drugs.

The invention provides the use of hydrogel comprising cellulose nanofibers and/or derivatives thereof as a carrier for drug delivery compositions.

The present invention also relates to a method for producing a composition according to the invention, comprising the steps of providing cellulose nanofibers and/or derivatives thereof; mixing together said cellulose nanofibers and/or derivatives thereof with water; and combining the obtained mixture with at least one suitable medicament or drug substance.

The drug substance may be incorporated in the hydrogel as an aqueous solution or dispersion. Preferably sterile or pharmaceutical grade water is used.

The obtained composition (mixture) comprising the drug substance or medicament may be placed or transferred to a suitable environment or device for drug delivery, such as an applicator, syringe, kit or the like.

Said composition comprises suitably 0.05-20 wt % of cellulose nanofibers and 0.001-20 wt % of at least one drug substance or medicament and water.

The present inventors surprisingly found out that particularly the plant derived CNF hydrogel can be used without any modifications in drug delivery in vivo.

In topical drug delivery compositions plant derived cellulose and microbial cellulose may be used. In the injectable products it is preferable to use plant derived cellulose, particularly preferably native or non-ionic grade.

The removal of cellulose nanofibers from the composition may be carried out for example with enzymes using enzymatic degradation of cellulose molecules. Proper enzymes are for example commercially available cellulases.

The present invention discloses particularly the physical and biocompatibility properties of plant derived CNF hydrogel. Plant cellulose is extensively used in the paper and textile industry and is abundant naturally. The native cellulose nanofiber hydrogel is opaque. Chemical modification of cellulose pulp prior to mechanical disintegration gives rise to optically transparent hydrogels.

Cellulose nanofibers of the present invention can be used in the form of hydrogel or dry or wet membrane. The gel strength of CNF hydrogel can be easily altered by dilution. Cellulose nanofibers or a derivative thereof having similar properties is not toxic to cells.

If cellulose nanofiber hydrogels are compared to UV cross-linkable cell culture hydrogels, like hyaluronic acid or PEG hydrogels, the CNF materials are considered much less toxic. In UV cross-linkable gels harmful photoinitiators are needed to initiate gelation while the CNF hydrogels are formed spontaneously. The non-covalent nature of the CNF hydrogels allows also adjustment of the porosity by dilution.

The remarkably high yield stress stabilizes the composition against sedimentation.

Bacterial cellulose has been used directly after fermentation, in which case the resulting membrane structure is considerably firmer than the hydrogel of the present invention i.e. a hydrogel from cellulose nanofibers. Therefore prior art methods have required additional processes for making the hydrogel matrix more porous.

The firmness of the cell culture media containing cellulose nanofibers in gel form can be adjusted without influencing the properties of the cell culture. Cellulose nanofibers originating from bacteria are also thicker than cellulose nanofibers from other sources.

The material of the invention may be injectable or sheet-like membrane with appropriate surface topology.

The properties of CNF are: transparent, non-toxic, highly viscous, high suspending power, high water retention, good mechanical adhesion, non-animal based, resembles ECM dimensions, insensitive to salts, temperature or pH, not degradable, no autofluorescence. CNF has negligible fluorescence background due to the chemical structure of the material. Furthermore, CNF gel is not toxic to the cells. Thus CNF gels are safe to be used as injectable and topical products to humans and animals.

Based on the diffusion studies the CNF hydrogel is highly permeable and is freely facilitating the exchange of oxygen, nutrients and water soluble metabolites of the cells.

Cryo transmission electron microscopy shows that the CNF hydrogel is composed of a mixture of individual cellulose nanofibrils and fiber bundles. The dimensions of CNF are alike native human collagen, which is a natural ECM component and commonly used as a cell support. The strength (elasticity) of CNF hydrogel stays nearly constant as function of used frequency from 0.01 to 1 Hz. Rheology data reveals the shear viscosity of about several hundred kilo Pascals in rest (low shear stress) to drop to few Pascals within one Pascal shear stress. That behavior is rather unique for biomaterial hydrogels. It enables the extremely good suspending capacity and by the shear-thinning behaviour enables the desired easy dispensing and injection independently of the size of the used needles. The mechanical properties of elasticity and stiffness are optimal for CNF hydrogels and injection.

The dimensions of the fibrillar network of cellulose nanofibers or a derivative thereof is very close to natural ECM network of collagen nanofibers. Furthermore, cellulose nanofibers or a derivative thereof is non-animal based material, i.e. there is no risk for disease transfer. Currently, most of the commercial products are isolated from animals. Possibilities to adjust physical form: CNF materials from hydrogels to membranes can be utilized. CNF membranes are transparent and highly porous. Mass production is easy compared to alternatives.

Native cellulose nanofibers are not toxic to the cells. Cellulose nanofibers or a derivative thereof have neglible fluorescence background. Cellulose nanofiber hydrogel has optimal elasticity, stiffness, shear stress, mechanical adhesion and porocity.

In an aqueous environment, cellulose nanofibers form a continuous hydrogel network of dispersed nanofibers or nanofiber bundles. The gel is formed by highly hydrated fibrils that are entangled between each other, even at very low concentrations. The fibrils may interact also via hydrogen bonds. The macroscopic structure is easily destroyed with mechanical agitation, i.e. the gel starts to flow at elevated shear stress. Cellulose nanofiber hydrogels and/or derivatives thereof have not been previously described to be used as cell culture material.

Applications of the present invention include providing drug dosage applications, biotechnological or biological medicines and their dosage. The unique rheological properties of the CNF hydrogel enables several applications which are based on the injectability of the hydrogel, like injection of drugs in CNF hydrogel in intraocular, intramuscular, or subcutaneous treatments, as well as topical products.

The following examples are given to further illustrate the invention and are not intended to limit the scope thereof. Based on the description, a person skilled in the art will be able to modify the invention in many ways.

EXAMPLES

Materials and Methods
Preparation of CNF Hydrogels

Figure 1:
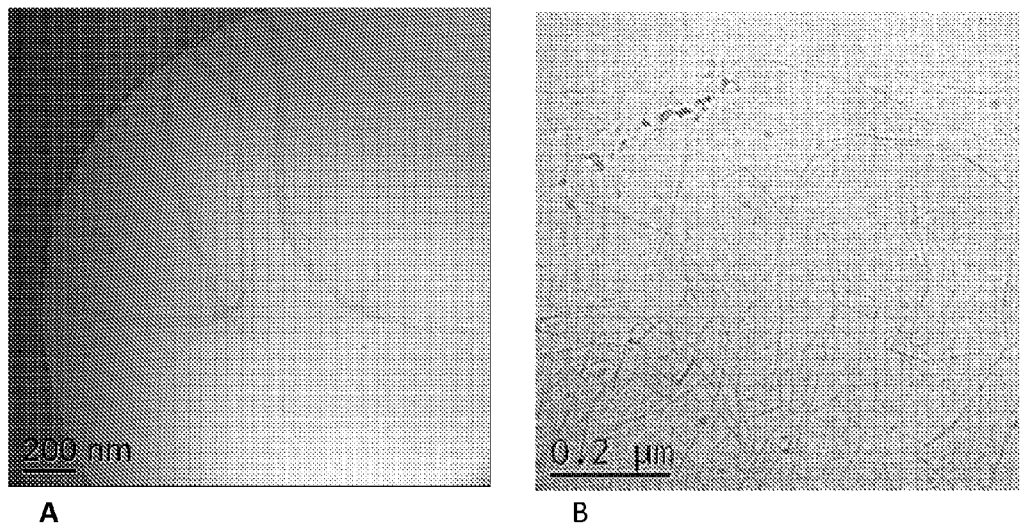
FIG. 1 depicts cryo-TEM images of cellulose nanofiber hydrogels. Native CNF is on the left side (A) and transparent CNF is on the right side (B).

The opaque native CNF hydrogel (1.7 wt %) was obtained by high pressure homogenization of wet cellulose pulp fibers. Thus, the direct product from the process is a dilute cellulose nanofiber hydrogel. The transparent CNF hydrogel (0.9 wt %) was obtained by similar homogenization process of a chemically modified (TEMPO-oxidized) cellulose pulp. The samples were autoclave sterilized. For the cell studies, the CNF hydrogel was diluted to proper concentration and homogenized with mechanical mixing or sonication. Cryo-TEM images of native CNF and transparent CNF are presented in FIG. 1. Native, cellulose nanofiber hydrogel is composed of a mixture of individual cellulose nanofibrils and fiber bundles (FIG. 1A). The diameter of smallest fibers is approximately 7 nm, majority of the cellulose material is forming 50-100 nm in bundled structures, however. The exact length scale can not estimated from the images due to entangled and bundled nature of the material, but it seems clear that individual nanofibers are several micrometers long. The cryo-TEM image of the optically transparent CNF hydrogel shows homogeneously distributed individual cellulose nanofiber network. The diameter of these nanofibers is approximately 7 nm and the length exceeds a micrometer. The nanofibers have 100-200 nm long straight segments followed by sharp kinks along the fiber axel. These straight segments are composed of highly crystalline cellulose domains—the bending sites are formed by the amorphous parts.

Preparation of CNF Membranes

CNF membranes were prepared by vacuum filtration of an aqueous 0.2 wt % native CNF dispersion. After filtration, the wet membranes were dried under weight in oven at 55° C. for 48 h. The dry films were smooth and opaque with the grammage of 70-80 g/m$^2$.

Enzymatic Hydrolysis

Enzymatic degradation of CNF hydrogels was demonstrated by hydrolyzing gravel containing 0.5% hydrogels with Celluclast 1.5 LFG, CCN0367 (Novozymes, pHopt 5), Prot. 90 mg/ml. Degradation of native CNF was conducted at pH 5 at 50° C. for 4 days and degradation of transparent CNF at pH 7 at 21° C. for one hour. Enzyme dosage was 5 mg of enzyme to one gram of CNF.

Background fluorescence measurements (negative control) were determined from wells containing hydrogel and dye reagent in culture medium but no cells. The mean and standard deviation for all fluorescence measurements were calculated and subsequently corrected for background and expressed as relative fluorescence.

Example 1

Diffusion of Dextrans Through CNF Hydrogels

Detailed knowledge on the diffusion properties of a material is important. The cell culture material should be porous enough to allow diffusion of nutrients and oxygen to the cultured cells as well as to enable efficient diffusion of metabolites from the cells. The diffusion properties of CNF hydrogel was demonstrated with different molecular weight dextrans in the following manner:

400 µl of transparent or opaque CNF (1%) was planted per filter on the apical compartment in Transwell™ filter well plates (filter pore size 0.4 µm). 1 ml of PBS was added into the basolateral side and 100 µl (25 µg) of fluorescent labeled dextrans were added on top of the hydrogels (MW of 20k, 70k and 250k). Plate was fixed firmly and left undisturbed on a well plate rocker. 100 µl samples were taken from the basolateral side and equal amount was replaced with PBS. First samples were taken with 15 minute intervals, other samples were taken with different time points ranging from 30 minutes to 2 hours and final samples at 24 hours. Total of 168 samples were taken. Target plate (OptiPlate™-96 F) was measured at excitation and emission wavelengths 490 nm and 520 nm respectively.

Figure 2:
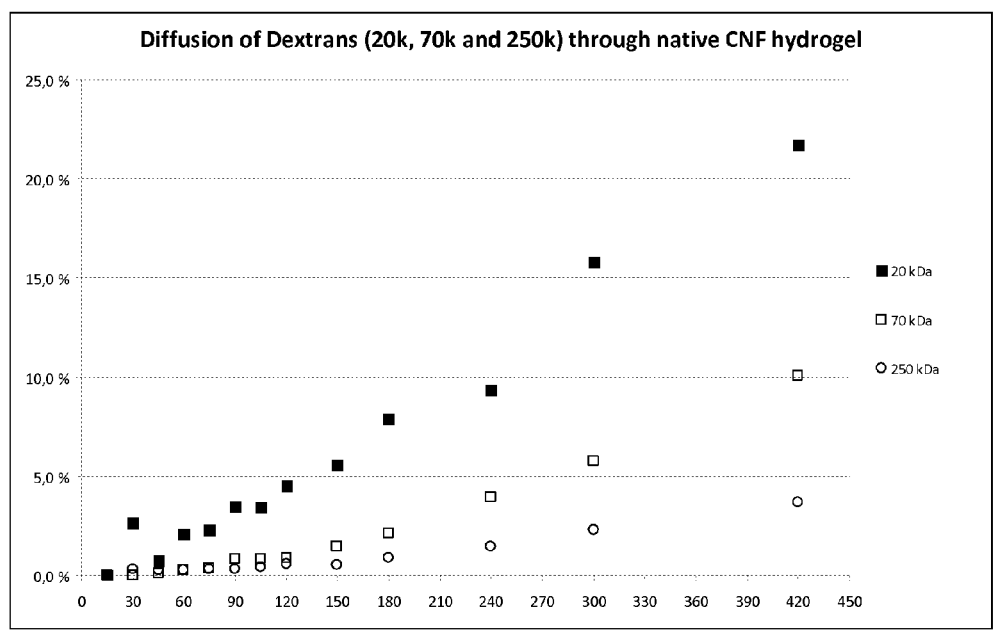
FIG. 2 depicts diffusion of different molecular weight dextrans (20 kDa, 70 kDa, and 250 kDa) through 1% native cellulose nanofiber hydrogel.

Diffusion of different molecular weight dextrans through 1% native cellulose nanofiber gel is presented in FIG. 2. The diffusion of the model compounds takes place at constant rate and it is highly dependent on the molecular weight (size) of the compound. It is clear that in the CNF hydrogels molecules are able to diffuse efficiently although the gel structure is firm enough to stabilize the cell suspension.

The observed diffusion profile can be utilized in various drug delivery formulations and applications. The diffusion of drugs can be controlled as a function of the size of the drug molecule or protein (used as drug) or as a CNF hydrogel concentration. The clear sustained release profile is especially beneficial for certain treatments where longer release is preferred, especially in the case of peptide or protein drugs.

Example 2

Gel Strength

Figure 3:
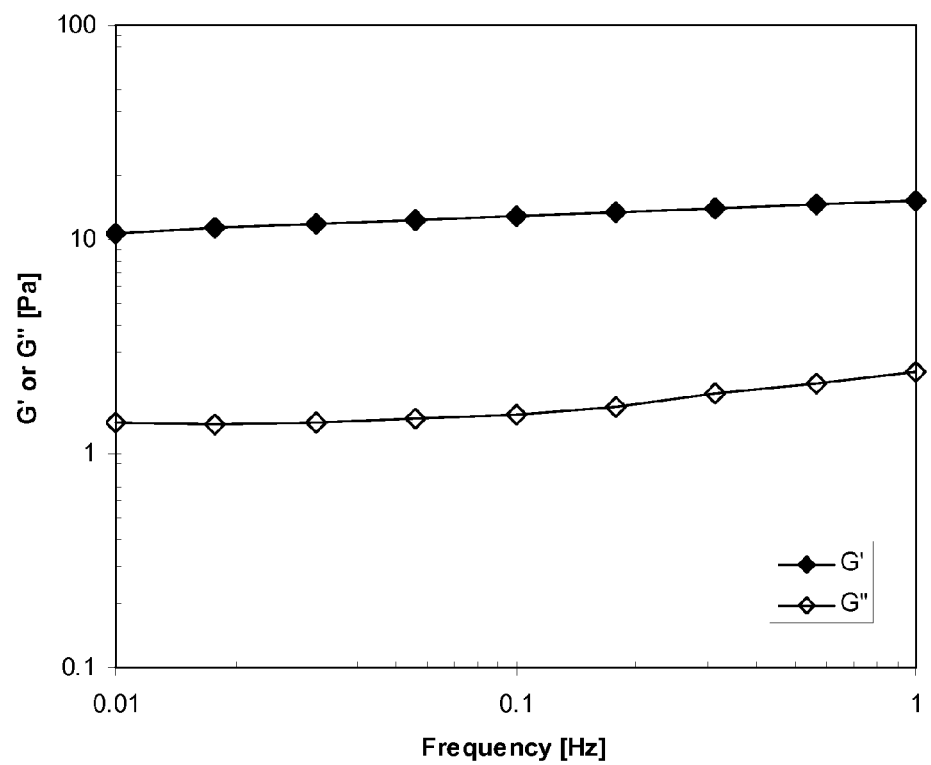
FIG. 3 depicts visco-elastic properties of 0.5% CNF hydrogel by dynamic oscillatory rheological measurements. Frequency dependence of G' (the storage modulus) and G" (the loss modulus) of a 0.5% native CNF hydrogel are presented.

An important function of a medium is to prevent sedimentation. CNF fulfills this demand by its ability to form a gel network at very low concentration (0.5%). The gel-like structure of CNF was shown by determining its viscoelastic properties by dynamic oscillatory rheological measurements. The results from the frequency sweeps show typical gel-like behavior. The storage modulus (G') is several orders of magnitude higher than the loss modulus (G') and nearly independent of frequency, which means that elastic (solid-like) properties are more pronounced than viscous (liquid-like) characteristics (FIG. 3). Typical for gels is also that both G' and G" are relatively independent of frequency. The viscoelastic properties of the CNF gels were determined with an oscillatory frequency sweep measurement in a rheometer (AR-G2, TA Instruments) at a strain of 0.1%.

Example 3

Flow Properties of CNF Hydrogel

The rheological flow properties of CNF hydrogels result in several beneficial features. The hydrogels have a high viscosity at low shear (or rest) for optimum suspending capacity of the cells but also show shear-thinning behavior at higher shear rates to enable easy dispensing and injection. The ability of CNF to provide these kinds of rheological properties was demonstrated in a test series where the viscosity of CNF dispersions was measured over a broad shear stress (rate) range in a rotational rheometer (AR-G2, TA Instruments, UK).

Figure 4:
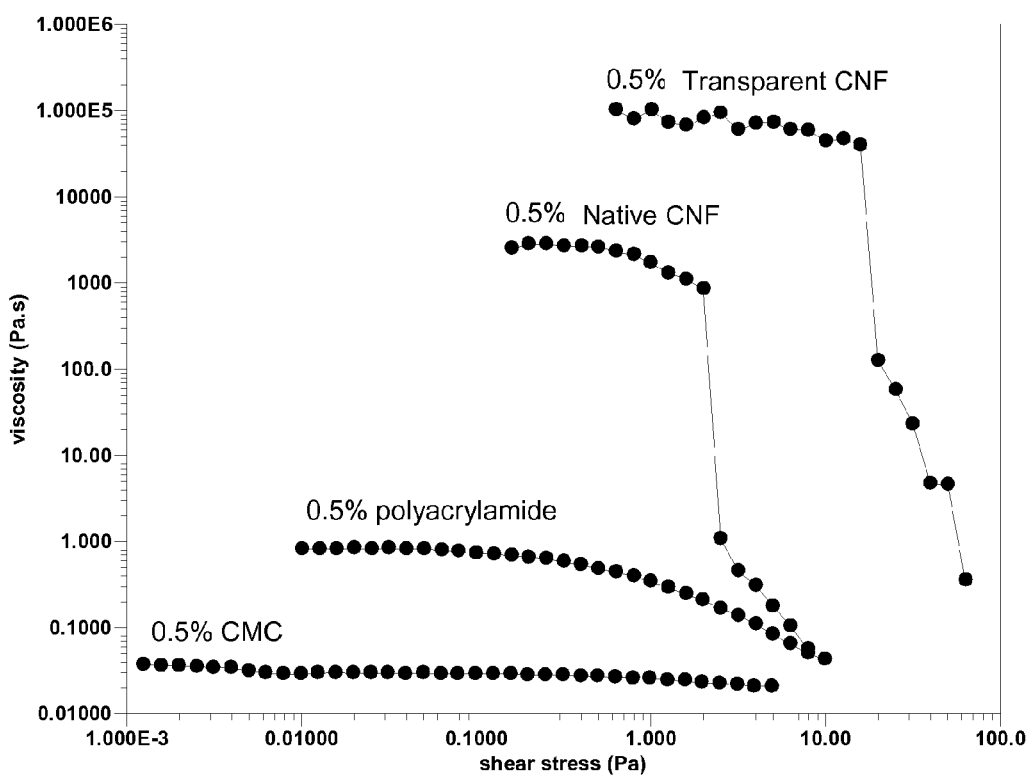
FIG. 4 depicts viscosity of 0.5% CNF hydrogels as function of applied shear stress in comparison with 0.5% solution of water soluble polymers polyacrylamide (5 000 kDa) and CMC (250 kDa).

CNF dispersions show much higher zero-shear viscosities (the region of constant viscosity at small shear stresses) than other water soluble polymers, as shown in FIG. 4. The zero-shear viscosity of CNF is greatly increased by smaller nanofibril diameter induced by preceding chemical pretreatment of the starting material. The stress at which shear-thinning behavior starts ("yield stress") is also considerably high for the CNF dispersions. The suspending ability of a material is the better the higher the yield stress. For example cells are effectively stabilized against sedimentation by the combined effects of high zero-shear viscosity and high yield stress and high storage modulus. The gravitational force applied by the cells is much weaker than the yield stress. Thus, the suspended cells are "frozen" inside the gel matrix if mixing with CNF or "frozen" on the gel if deposited on the top of the gel.

Figure 5:
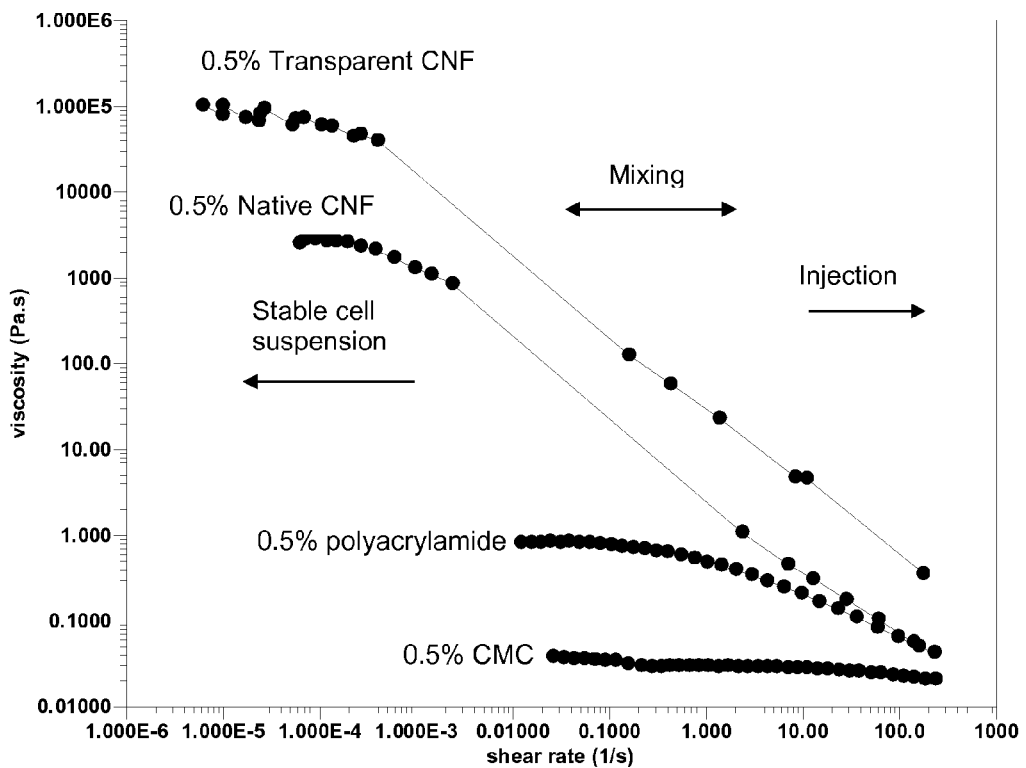
FIG. 5 depicts viscosity of 0.5% CNF hydrogels as function of measured shear rate in comparison with 0.5% polyacrylamide and CMC. Typical shear rate regions of different physical processes have been marked on the figure with arrows.

In FIG. 5 the viscosity is presented as a function of the measured shear rate. From this FIG. 5 it is obvious that the viscosity of the CNF dispersions drops at relatively small shear rates and reaches a similar level as that measured for the reference materials at shear rates of about 200 s$^{-1}$.

The network structure of CNF breaks down upon shearing (FIG. 4). Upon the application of a certain stress, the viscosity of the system drops dramatically and a transition from solid-like to liquid-like behavior occurs. This kind of behavior is beneficial as it enables mixing of for example cells homogeneously into the CNF suspension by moderate mechanical shearing. When two-phase liquids, such as flocculated CNF dispersions, are sheared (e.g. in a rheometer or in a tube), the dispersed phase tends to move away from the solid boundaries, which leads to the creation of a lower-viscosity layer of liquid at the walls of the container (FIG. 6). This phenomenon means that the resistance to flow, i.e. the viscosity is lower at the boundaries than in the bulk of the dispersion (Barnes, 1995). Respectively, injection of the CNF hydrogel with a syringe and a needle or with pipette is easy even at high concentrations (1-4%). The phenomenon enables also easy dispensing of cell suspensions with minimum disturbance of the cells, i.e. majority of the cells are located in the middle of the needle and are practically at rest (FIG. 6).

Easy injectability of the CNF hydrogels is also important feature when injectable drug formulations are considered. As was described in Example 1, the CNF hydrogels have release profiles that could be utilized in sustained and controlled drug release applications. These two findings for CNF hydrogels enable various potential drug treatment applications, like intraocular, intramuscular, subcutaneous treatments or for example viscoelastic eye drop formulations.

Example 4

Structure recovery after shearing has ceased An additional important rheological property of CNF hydrogels is that the high level of viscosity is retained after shearing (e.g. injection or mixing) has ceased. The structure recovery of CNF dispersion was demonstrated by a test series where the material was first sheared in a rheometer (StressTech, Reologica Instruments Ab) at a high shear rate and after stopping the shear the recovery of the gel strength (G') was monitored with an oscillatory time sweep measurement. The shearing cycle was performed in concentric cylinder geometry at a constant stress of 40 Pa for 61 s. The evolution of shear rate and viscosity during this test is shown in FIG. 7. The material was sheared at a relatively high shear rate (1000 s−1) for a time period of at least 40 s, during which the viscosity of the material dropped below 40 mPa s.

After stopping the shear, the evolution of G' (a measure of gel strength) was followed by an oscillatory measurement at constant frequency (1 Hz) and small stress (0.5 Pa). The measurement was started exactly 10 s after the shearing was stopped. From FIG. 8 it is obvious that a gel network is very rapidly formed when the CNF dispersion is allowed to rest after it has been sheared at high shear rates. Substantial structure recovery is observed already 10 s after the cessation of shear (equal to time zero in FIG. 8). A constant storage modulus (G') level is reached after keeping the CNF dispersion at rest for less than 10 min. The G'-level that the extensively sheared CNF dispersion developed was comparable to that of a CNF dispersion that was only gently mixed with a glass rod before the structure recovery test.

Evolution of shear rate and viscosity when a 0.7% native CNF dispersion was sheared in a rheometer in concentric cylinder geometry at a constant stress of 40 Pa is presented in FIG. 8.

Structure recovery of a 0.7% native CNF dispersion after shearing at high shear-rate as compared with after gentle mixing with a glass rod is presented in FIG. 8.

The fast structure recovery is important for hydrogel-type cell culture materials for two reasons. Firstly, it enables cells to be homogeneously distributed in the CNF hydrogels after mixing them with the hydrogel. Secondly, if the CNF hydrogels are used to transport cultured cells, the fast recovery of the gel structure effectively traps the cells to the desired place and the migration is minimal, for example when in cell transplantation is considered. Fast recovery is essential also in the injectable drug release formulations.

Example 5

Stability

Even very dilute dispersions of CNF have a very high viscosity at low shear rates. The hydrogel structure is also recovered when shear, such as injection, ceases. At static conditions, CNF forms a hydrogel network with high elastic modulus and exceptionally high yield stress. Due to these properties, CNF has a very high suspending power of solid particles even at very low concentration.

The suspending ability at static conditions is demonstrated with gravel suspensions. 0.5% dispersions of native CNF and transparent CNF are able to stabilize even 2-3 mm size gravel particles for very long periods of time, see FIG. 9. It should be noted that the transparent CNF is able to stabilize particle suspensions at lower concentration than native CNF.

Example 6

Enzymatic Hydrolysis

It is commonly known that certain enzymes, cellulases, are able to hydrolyse β-(1-4)-bonds in cellulose. For example endo-1,4-β-glucanases (EGs) that target cellulose chains in random locations away from the chain ends; exoglucanases or exocellobiohydrolases (CBHs) that degrade cellulose by splitting off molecules from both ends of the chain producing cellobiose dimers; and β-glucosidases (BGLs) that hydrolyze the cellobiose units (produced during EG and CBH attack) to glucose. Respectively, cellulose nanofibers can be enzymatically hydrolyzed to glucose with an aid of cellulases (Ahola, S., Turon, X., Osterberg, M., Laine, J., Rojas, O. J., Langmuir, 2008, 24, 11592-11599).

Enzymatic hydrolysis of cellulose can be utilized in cellulose nanofiber containing cell culture systems for various reasons. Upon the hydrolysis of CNF hydrogel, the viscosity of the media is drastically lowered and the cultured cell structures are easily accessible e.g. for staining. Also, after the hydrolysis, the cell structures can be transferred or transplanted without the cellulose containing material. The degradation product, glucose, is generally non-toxic to cells and can be utilized as a nutrient in cell culturing.

The enzymatic hydrolysis of cellulose nanofibers can be conducted with an aid of different cellulases at different environment. In FIG. 10, the effect of commercial Celluclast enzymes on the suspending power of the gels is demonstrated. Both native and transparent CNF hydrogels loose the suspending power due to enzymatic degradation of the gel structure. The cultured cell lines can be also genetically engineered to produce the needed enzyme protein into the culture system.

Example 7

Ophthalmic Composition

A 0.5 wt % hydrogel based on native cellulose nanofibers is made using purified water. 0.1 wt % of hyaluronic acid, 0.1 wt % of EDTA, 0.2 wt % of propyl paraben, 0.2 wt % of Tween 80 and 0.8 wt % of glycerol are incorporated in the hydrogel to obtain a homogeneous dispersion suitable for ophthalmic use. Alternatively, the ingredients may be incorporated in purified water, which is subsequently mixed with the cellulose nanofibers. In a similar manner, compositions comprising for example agents for controlling retinal pressure or for other indications can be obtained.

Example 8

Local Anesthetic Composition

A 1.2 wt % hydrogel based on native cellulose nanofibers is made using purified water. 0.2 wt % of propyl paraben and 15 wt % of benzocaine is incorporated in the hydrogel with ethanol for assisting the dissolution of the drug. Alternatively the drug substance may be dispersed in particulate form in the hydrogel without the alcohol whereby controlled release of the drug is achieved.

The invention claimed is:

1. A drug delivery composition, characterized in that the composition comprises plant derived cellulose nanofibers and/or derivatives thereof and a drug or medicament, wherein the plant derived cellulose nanofibers and/or derivatives thereof are in the form of a hydrogel and said cellulose nanofibers are obtained by mechanical disintegration, said hydrogel being a direct product of homogenization of said cellulose nanofibers, wherein the delivery of the drug or medicament is controlled by diffusion through the hydrogel.

2. The composition according to claim 1, characterized in that the cellulose nanofiber derivatives comprise chemically or physically modified derivatives of cellulose nanofibers or nanofiber bundles.

3. The composition according to claim 1, characterized in that the composition is a topical, subcutaneous, intramuscular or intraocular composition.

4. The composition according to claim 1, wherein the drug or medicament is incorporated in the hydrogel as an aqueous solution or dispersion.

5. The composition according to claim 1, wherein the composition comprises about 0.05-20 wt percent of cellulose nanofibers and about 0.001-20 wt percent of the drug or medicament and water.

6. The composition according to claim 1, wherein the composition is injectable.

7. The composition according to claim 6, wherein the plant derived cellulose is native grade.

8. The composition of claim 1, wherein the cellulose nanofibers are configured to form a gel network at 0.5% by weight.

9. The composition of claim 1, wherein the composition comprises 0.5-4% by weight of plant derived cellulose nanofibers and/or derivatives thereof.

10. The composition of claim 1, wherein the diameter of cellulose nanofibers and/or derivatives thereof or nanofiber bundles in the cellulose nanofibers is less than 200 nm.

11. The composition of claim 1, wherein the diameter of cellulose nanofibers and/or derivatives thereof or nanofiber bundles in the cellulose nanofibers is less than 100 nm.

12. The composition of claim 1, wherein the diameter of the cellulose nanofibers and/or derivatives thereof is less than 1 μm.

13. The composition of claim 1, wherein the hydrogel is configured to be used without any substantial modifications in drug delivery in vivo.

14. The composition of claim 1, wherein the storage modulus of the hydrogel is at least one order of magnitude higher than the loss modulus of the hydrogel.

15. The composition of claim 1, wherein the hydrogel is opaque, and the homogenization includes high pressure homogenization of the cellulose nanofibers, the cellulose nanofibers being wet cellulose nanofibers.

16. The composition of claim 1, wherein the hydrogel is transparent, and the cellulose nanofibers are chemically modified.

* * * * *